United States Patent [19]
Kane et al.

[11] Patent Number: 5,260,450
[45] Date of Patent: Nov. 9, 1993

[54] 3-ARYL-5-ALKYLTHIO-4H-1,2,4-TRIAZOLES

[75] Inventors: John M. Kane, Cincinnati; Francis P. Miller, Loveland, both of Ohio

[73] Assignee: Merrell Dow Pharmaceuticals Inc., Cincinnati, Ohio

[21] Appl. No.: 928,256

[22] Filed: Aug. 11, 1992

Related U.S. Application Data

[60] Division of Ser. No. 770,837, Oct. 4, 1991, Pat. No. 5,143,933, which is a continuation-in-part of Ser. No. 630,659, Dec. 20, 1990, abandoned, which is a continuation-in-part of Ser. No. 463,082, Jan. 10, 1990, Pat. No. 4,981,863, which is a division of Ser. No. 126,191, Dec. 4, 1987, Pat. No. 4,900,743, which is a continuation-in-part of Ser. No. 7,063, Jan. 27, 1987, abandoned.

[51] Int. Cl.$^5$ .......................... C07D 249/12
[52] U.S. Cl. ................................. 548/264.4
[58] Field of Search ..................... 548/264.4

[56] References Cited

PUBLICATIONS

Journal of Medicinal Chemistry, vol. 14(3), pp. 260–262 (1971), Mhasalkar, M. Y., et al.
Boll. Chim. Farm., 108 (1969), pp. 128–139, Russo, F., et al.
Deliwala et al, "Further Studies in substituted, etc" CA 74:111968u (1971).
Russo et al, "1,2,4-Triazole Derivatives" CA71:49853k (1969).

Primary Examiner—Patricia L. Morris

[57] ABSTRACT

This invention relates to novel sulfone and sulfoxide derivatives of 3-aryl-5-alkylthio-4H-1,2,4-triazoles and to the use of 3-aryl-5-alkylthio-, alkylsulfinyl- and alkylsulfonyl-4H-1,2,4-triazoles in the treatment of patients suffering from convulsant seizures.

12 Claims, No Drawings

3-ARYL-5-ALKYLTHIO-4H-1,2,4-TRIAZOLES

This is a division of application Ser No. 07/770,837, filed Oct. 4, 1991, now U.S. Pat. No. 5,143,933, which is a continuation-in-part of copending application Ser. No. 07/630,659, filed Dec. 20, 1990, now abandoned, which is a continuation-in-part of application Ser. No. 07/463,082, filed Jan. 10, 1990, now U.S. Pat. No. 4,981,863, which is a division of application Ser. No. 07/126,191, filed Dec. 4, 1987, now U.S. Pat. No. 4,900,743, which is a continuation-in-part of application Ser. No. 07/007,063, filed Jan. 27, 1987, now abandoned.

SUMMARY OF THE INVENTION

This invention relates to derivatives of 3-aryl-5-alkylthio-4H-1,2,4-triazoles and their use in the treatment of patients suffering from muscle tension, muscle spasms and the pain associated therewith, chronic hyperreflexia due to spinal trauma, convulsant seizures and anxiety.

More specifically this invention relates to the use of compounds of formula I

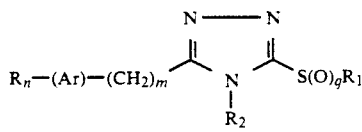

wherein
Ar is phenyl or naphthyl;
$R_1$ is $C_{1-6}$ lower alkyl;
$R_2$ is hydrogen or $C_{1-6}$ lower alkyl;
R is $C_{1-6}$ lower alkyl, $C_{1-6}$ alkoxy, hydroxy, halogeno, or trifluoromethyl and n is zero, 1 or 2, or $R_n$—(Ar) is methylenedioxyphenyl; and each of m and q is zero, 1 or 2;
and their pharmaceutically acceptable salts as muscle relaxants, antispastics, anticonvulsants and anxiolytics.

Another aspect of this invention relates to novel 5-aryl-3-alkylsulfinyl-4H-1,2,4-triazoles of formula II,

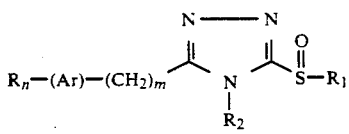

wherein Ar, $R_1$, $R_2$, R, m and n have the meanings defined above.

Another aspect of this invention relates to novel 5-aryl-3-alkylsulfonyl-4H-1,2,4-triazoles of formula III,

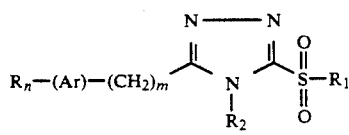

wherein Ar, $R_1$, $R_2$, R, m and n have the meanings defined above, with the provisos that (1) $R_n$—Ar—$(CH_2)_m$ is other than 2-ethoxyphenyl; that (2) when $R_n$—(Ar)—$(CH_2)_m$ is phenyl and $R_1$, is methyl, $R_2$ is $C_{1-6}$ lower alkyl; and that (3) when $R_n$—(Ar)—$(CH_2)_m$ represents 4-chlorophenyl, $R_2$ is other than ethyl.

DETAILED DESCRIPTION OF THE INVENTION

In Formulas I, II and III, halogeno preferably represents chloro or fluoro, and methyl and ethyl are the preferred lower alkyl moieties, although all the straight and branched manifestations thereof are included. Lower alkoxy radicals include ethers having alkyl moieties paralleling the $C_{1-6}$ alkyl group. When "Ar" is phenyl, n is preferably one, representing a mono-substituted phenyl moiety with the R-substituent being a group located at any of the ortho, meta or para positions. When n is 2, the 2,3-, 2,4-, 2,5-, 2,6-, 3,4-, or 3,5-positions are contemplated. Preferably $R_1$, and R2 each represents methyl or ethyl.

State of the art salts of these triazoles may be employed, with the hydrochloride being one of convenience and general applicability. These salts are formed by standard techniques well known in the art.

When "Ar" represents naphthyl, the naphthyl ring system can be bonded through the 1- or 2- position and the R moiety can be attached thereto at any of the available positions.

The thioethers of Formula I may be prepared using processes and procedures analogously known in the art as depicted in Reaction Scheme A, wherein $R_1$, R2 and $R_n$—(Ar)—$(CH_2)_m$ are as defined for Formula I, and X is a suitable leaving group.

Reaction Scheme A:

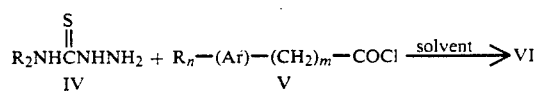

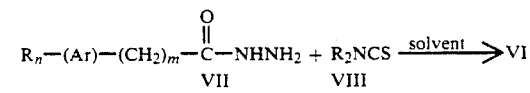

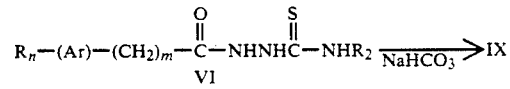

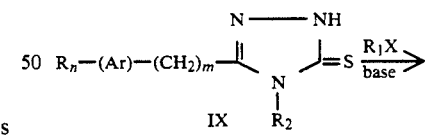

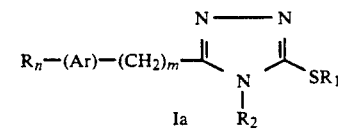

The sulfoxides and sulfones of Formula I may be prepared by oxidizing the alkylthioethers of Formula Ia with a peracid, preferably M-chloroperoxybenzoic acid (MCPBA), as seen in the following Reaction Scheme B, wherein, $R_1$, $R_2$ and $R_n$—(Ar)—$(CH_2)_m$ are as defined for Formula I.

Reaction Scheme B:

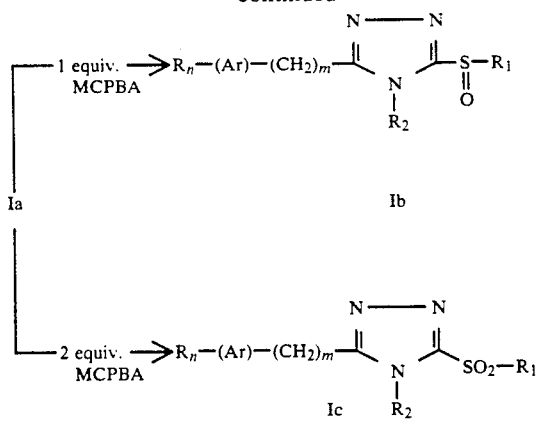

The preparation of the $R_2$-substituted thiosemicarbaides (IV) is readily effected by reacting hydrazine with an isothiocyanate in a suitable solvent. The reaction is quite rapid and may be carried out between 0° C and room temperature. Although the reaction proceeds rapidly, the mixture may be left for up to 24 hours without significant decrease in yield. Reflux conditions may be employed but are not preferred. Almost all solvents may be used. Alcohols (preferably ethanol or methanol) are preferred, although dimethylformamide (DMF), $CHCl_3$, $CH_2Cl_2$, tetrahydrofuran (THF) and $Et_2$ may also be used. The required isothiocyanates are generally commercially available but may also be prepared by known techniques quite obvious to one of ordinary skill in the art. Once obtained, the thiosemicarbazides are converted to their corresponding aroyl-substituted thiosemicarbazides (VI) by reaction with an appropriate acid chloride (V) in an aprotic solvent such as pyridine, $CHCl_3$, THF, and the like. The acylation proceeds rather easily at temperatures ranging from 0° C to room temperature over periods of 3 to 24 hours, although elevated temperatures (e.g., reflux temperatures) may be employed. Alternatively, aroyl-substituted thiosemicarbazides (VI) may also be prepared by reacting carboxylic acid hydrazides (VII) and isothiocyanates (VIII) in an aprotic solvent such as THF, $CHCl_3$, $CH_2Cl_2$, and the like. Again, the acid halides (V) and acid hydrazides (VII) are often commercially available, but may also be prepared from the corresponding acids which are generally commercially available.

The aroyl thiosemicarbazides (VI) are subjected to a cyclization reaction which yields 3-aryl-3H-1,2,4-triazole-5-thiones of formula IX. The cyclization reaction is effected by heating the compounds (VI) in an aqueous base such as sodium bicarbonate or sodium hydroxide. Alcoholic bases may be utilized but generally are less desirable. The reaction is conducted at about the reflux temperature of the solvent, preferably at about 65°–100° C.

The preparation of the alkylthioethers (Ia) is readily effected by standard alkylation procedures. Preferably the 3-aryl-3H-1,2,4-triazole-5-thiones (IX) are reacted with the appropriate alkyl halide ($R_1,X$) or a functional equivalent thereof in the presence of a mild base. Suitable bases are alkali metal carbonates or bicarbonates or alkali metal hydroxides, with $K_2CO_3$ or aqueous NaOH being preferred. It is preferred to use an alkyl iodide for the alkylation reaction, but any suitable leaving group (e.g., bromide or—$OSO_2CF_3$) may be used instead of the iodide. Suitable solvents are acetone, aqueous ethanol, tetrahydrofuran (THF), pyridine, and the like. The reaction may be carried out at temperatures ranging from room temperature to the reflux temperature of the reaction mixture, and in general the reaction takes about 15 hours or longer.

The conversion of the 3-aryl-4-alkyl-5-alkylthio-4H-1,2,4-triazoles (Ia) to their higher oxidation state is preferably effected by oxidizing the alkylthioethers (Ia) with a peracid according to well known conditions. Suitable oxidizing agents are $H_2H_2$ and $NaIO_4$, but m-chloroperoxybenzoic acid is preferred. In effecting the oxidation to the sulfinyl derivatives of Formula Ib, 1 molar equivalent of the peracid is used while 2 equivalents of the peracid will yield the sulfonyl derivatives of Formula Ic. The oxidations are carried out at temperatures of about 0° C. to room temperature in solvents which themselves are not susceptible to oxidation. Preferred solvents are $CH_2Cl_2$, $CHCl_3$, and acetic acid.

Thioethers of Formula Ia have previously been found to be useful as pesticides, bactericides and fungicides, but have not previously been shown to possess muscle relaxant, antispastic, anticonvulsant or anxiolytic activity. 3-(4-Chlorophenyl)-4-ethyl-5-methylsulfonyl-4H-1,2,4-triazole was found by M. Y. Mhasalkar, et al. (J. Med 14(3), 260–2 (1971)), to have hypoglycemic activity, but neither that compound nor other sulfones of Formula Ic have previously been reported to have muscle relaxant, antispastic, anticonvulsant or anxiolytic activity.

It has now been discovered that previously known thioethers and sulfones of Formula I, as well as the novel sulfoxides and sulfones of Formulas II and III, exhibit pharmacological effects generally attributed to muscle relaxants, antispastics, anticonvulsants and anxiolytics, and thus the compounds of this invention will provide relief in patients suffering from muscle tension, muscle spasms and the pain associated therewith, convulsant seizures and anxiety. The compounds of this invention are also useful in treating hyperreflexia resulting from spinal injury, as claimed in copending application Ser. No. 630,666, filed Dec. 20, 1990.

Compounds that antagonize the tonic extensor seizures caused by strychnine have been shown to have muscle relaxant, antispastic, anticonvulsant and anxiolytic activities in man. The activity of the compounds can be demonstrated by the method of R. A. Turner, *Screening Methods in Pharmacology*, Chapter 14 (Academic Press, 1965). Groups of 10 to 20 male mice are administered one or more doses of test compound in an appropriate vehicle or, for comparison, the vehicle alone. At a selected time thereafter, strychnine sulfate, prepared as a solution in distilled water, is administered intraperitoneally at a dose of 2.7 mg/kg. Ninety-nine percent of vehicle-treated mice exhibit convulsions at this dose of strychnine. Absence of tonic extension for greater than 15 minutes after strychnine administration is considered significant protection.

Treatment of mice with a dosage range of baclofen, a known antispastic/muscle relaxant, of from 12.5 to 200 mg/kg i.p. causes over 50% antagonism of strychnine-induced seizures, but no dose causes 100% protection. Tizanidine, a known muscle relaxant, causes maximal protection of 60% at 3.1 mg/kg i.p., but doses of up to 50 mg/kg do not cause a greater effect. Diazepam, a known anxiolytic with muscle relaxant and anticonvulsant activity, causes a dose-related inhibition with an $ED_{50}$ of 1.2 mg/kg i.p.; however very high doses are required for total inhibition of strychnineinduced seizures. In contrast, many of the compounds of the present invention protect 100% against strychnine-induced seizures at doses in the range of 4 times the $ED_{50}$. Among the compounds of this invention, the intraperitoneally administered $ED_{50}$ is 14.4 mg/kg for 4-methyl-3-phenyl-5-ethylsulfinyl-4H-1,2,4-triazole; 19.3 mg/kg for 4-methyl-3-phenyl-5-ethylsulfonyl-4H-1,2,4-triazole; 12.8 mg/kg for 4-methyl-3-phenyl-5-methylsulfonyl-4H-1,2,4-triazole; and 18.6 mg/kg for 4-methyl-3-(2-fluorophenyl)-5-ethylthio-4H-1,2,4-triazole; while the orally administered $ED_{50}$ is 8.1 mg/kg for 4-methyl-3-phenyl-5-ethylsulfinyl-4H-1,2,4-triazole; 8.5 mg/kg for 4-methyl-3-phenyl-5-ethylsulfonyl-4H-1,2,4-triazole; 7.3 mg/kg for 4-methyl-3-phenyl-5-methylsulfonyl-4H-1,2,4-triazole; and 15.1 mg/kg for 4-methyl-3-(2-fluorophenyl)-5-ethylthio-4H-1,2,4-triazole.

Injuries to the spinal cord produce a form of muscle spasticity known as hyperreflexia, which can be reduced by treatment with compounds such as clonidine, as described in animals by L. E. Tremblay and J. J. Bedard (Neuropharmacology 25 (1986), 41-46) and in humans by P. W. Nance, A. H.Shears and D. M. Nance (Paraplegia 27 (1989), 296-301). The use of clonidine for this indication is impractical, however, because of clonidine's well-known blood pressure lowering effect and CNS depressant action. Compounds of this invention are useful for treating chronic hyperreflexia without such side effects. The effectiveness of the compounds of this invention for treating muscle spasticity resulting from spinal trauma was tested in rats with heightened spontaneous hind limb movements. Four to six weeks before testing, anesthetized rats were spinally transected at the mid-thoracic level, resulting in this form of spontaneous limb activity. 4-Methyl-3-phenyl-5-methylsulfonyl-4H-1,2,4-triazole or clonidine were given intraperitoneally, and after 30-minutes reflex activity was measured in treated animals and untreated controls by a computerized apparatus designed to record, integrate and analyze this activity. As shown in Table I, below, substantial reduction in muscle spasticity was seen in rats treated with more than 5 mg/kg of 4-methyl-3-phenyl-5-methylsulfonyl-4H-1,2,4-triazole or 3.1 µg/kg of clonidine.

TABLE I

| 4-Methyl-3-phenyl-5-methylsulfonyl-4H-1,2,4-triazole | | Clonidine | |
|---|---|---|---|
| Dosage, mg/kg. ip | Integrated Activity, % of Control | Dosage, µg/kg. ip | Integrated Activity, % of Control |
| 5.0 | 137 ± 10 | 3.1 | 130.2 ± 43.9 |
| 10.0 | 42.9 ± 12.7 | 12.5 | 50.4 ± 9.8 |
| 20.0 | 75.3 ± 19.3 | 50.0 | 32.5 ± 9.5 |
| 40.0 | 51.3 ± 11.9 | | |

By contrast, reflex activity induced bu pulling one hindlimb was not reduced by the test compounds, suggesting that compounds of this invention have a relatively selective action on the spontaneous activity without generally affecting reflex mechanisms.

In their use, the compounds of this invention will exert a relatively quick onset of action and have a prolonged duration of activity. In general, the compounds will exert their therapeutic effects at dose levels of about 0.25-250 mg/kg of body weight per day although, of course, the degree of severity of the disease state, the age of the patient and other factors determined by the attending diagnostician will influence the exact course and dosage regimen suitable for each patient. In general the parenterally administered dose of the active compounds is about equivalent to that of the orally administered dose. The compounds have been demonstrated to have a low potential for depressant or ataxic side effects.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch in combination with binders such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthesic origin, for example, peanut oil, soybean oil and mineral oil. In general, water, saline, aqueous dextrose and related sugar solutions, ethanol, glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic ®, a silicone rubber manufactured by the Dow-Corning Corporation.

As is true in many classes of compounds with a pharmacological activity having a therapeutic end-use application, certain subgeneric groups and certain specific members of the class, because of their overall therapeutic index and their biochemical and pharmacological profile, are preferred. In this instance the preferred compounds of formula I are those wherein $R_1$ and $R_2$ groups are methyl or ethyl, those wherein the R substituent is chloro or fluoro, those wherein the $R_n$ substituent is a monochloro or a monofluoro substituent, those wherein n is zero, those wherein m is zero, and those compounds wherein Ar is phenyl. Specifically preferred compounds are:

4-methyl-3-phenyl-5-methylsulfonyl-4H-1,2,4-triazole,
5-ethylsulfinyl-4-methyl-3-phenyl-4H-1,2,4-triazole,
5-ethylsulfonyl-4-methyl-3-phenyl-4H-1,2,4-triazole,
4-methyl-5-methylsulfinyl-3-phenyl-4H-1,2,4-triazole,
5-ethylthio-3-(2-fluorophenyl)-4-methyl-4H-1,2,4-triazole,
3-(2-fluorophenyl)-4-methyl-5-methylsulfonyl-4H-1,2,4-triazole, 3-(2-fluorophenyl)-4-methyl-5-methylthio-4H-1,2,4-triazole, 3-(2-fluorophenyl)-4-methyl-5-methylsulfinyl-4H-1,2,4-triazole, 3-(4-fluorophenyl)-4-methyl-5-methylthio-4H-1,2,4-triazole, 3-(2-chlorophenyl)-4-methyl-5-methylthio-4H-1,2,4-triazole, 4-ethyl-3-(2-fluorophenyl)-5-methylthio-4H-1,2,4-triazole, and 5-ethylthio-4-methyl-3-phenyl-4H-1,2,4-triazole.

The following specific examples are given to illustrate the preparation of the compounds of this invention, although the scope of compounds exemplified is not meant to be limiting, this being so in view of the ease by which the compounds of formula I may be prepared by the general methods exemplified by employment of the necessary intermediates and solvents.

EXAMPLE 1

1-(2-Fluorobenzoyl)-4-methylthiosemicarbazide

To a stirred room temperature suspension of 4-methylthiosemicarbazide (7.9 g, $7.5 \times 10^{-2}$ mole) and $CHCl_3$ (190 ml), 2-fluorobenzoyl chloride (9.4 ml, $7.9 \times 10^{-2}$ mole) was added dropwise. After stirring overnight at room temperature, the precipitate was collected by filtration and the product was washed with two portions of $Et_2O$. Drying by suction gave a colorless powder which was used without further purification in the subsequent cyclization step.

Alternate procedure

To a stirred room temperature solution of 4-methylthiosemicarbazide (10.5 g, $100 \times 10^{-1}$ mole) and pyridine (250 ml), 2-fluorobenzoyl chloride (11.9 ml, $1.00 \times 10^{-1}$ mole) was added dropwise. After stirring overnight at room temperature the excess pyridine was evaporated at reduced pressure first on a rotary evaporator and then at high vacuum. This afforded a mixture of the desired product and pyridine hydrochloride which is used without further purification in the subsequent cyclization step.

EXAMPLE 2

4-Methyl-1-(2-naphthoyl)thiosemicarbazide

To a stirred room temperature solution of 4-methylthiosemicarbazide (5.91 g, $5.62 \times 10^{-2}$ mole) and pyridine (150 ml) was added 2-naphthoyl chloride (10.7 g, $5.61 \times 10^{-2}$ mole). After stirring overnight, the pyridine was evaporated at reduced pressure. The concentrate was treated with water and the undissolved product was collected by filtration and dried by suction. Crystallization from acetone/ethanol afforded off-white needles, Mp 211° C. (decomp).

EXAMPLE 3

5-(2-Fluorophenyl)-2,4-dihydro-4-methyl-3H-1,2,4-triazole-3-thione 1-(2-Fluorobenzoyl)-4-methylthiosemicarbazide (11.3 g, $4.97 \times 10^{-2}$ mole) or the aforementioned mixture of the above and pyridine hydrochloride and 1 molar aqueous $NaHCO_3$ (480 ml, $4.80 \times 10^{-1}$ mole) were stirred and heated to reflux. After refluxing overnight, the reaction was cooled in an ice bath before being acidified by the dropwise addition of concentrated hydrochloric acid (40 ml, $4.8 \times 10^{-1}$ mole). The resulting precipitate was collected by filtration, washed with a little $H_2O$, and dried by suction. This afforded a colorless powder. This material was of sufficient purity to go on to the next step. If desired this material could be crystallized from EtOAc/hexane affording colorless needles, Mp 137°-139° C.

EXAMPLE 4

2,4-Dihydro-4-methyl-5-(2-naphthyl)-3H-1,2,4-triazole-3-thione

4-Methyl-1-(2-naphthoyl)thiosemicarbazide (12.9 g, $4.97 \times 10^{-2}$ mole) and 1 molar aqueous $NaHCO_3$ (480 ml, $4.80 \times 10^{-1}$ mole) were stirred and warmed to reflux. After refluxing overnight, the reaction was cooled in an ice bath before being acidified by the dropwise addition of concentrated hydrochloric acid (40 ml, $4.8 \times 10^{-1}$ mole). The resulting product was collected by filtration and dried by suction. Crystallization from ethanol afforded beige needles, Mp 223°-225° C.

EXAMPLE 5

3-(2-Fluorophenyl)-4-methyl-5-methylthio-4H-1,2,4-triazole

A mixture of 5-(2-fluorophenyl)-2,4-dihydro-4-methyl-3H-1,2,4-triazole-3-thione (4.56 g, $2.18 \times 10^{-2}$ mole), $K_2CO_3$ (3.01 g, $2.18 \times 10^{-2}$ mole), methyl iodide (1.5 ml, $2.4 \times 10^{-2}$ mole), and acetone (65 ml) was stirred and warmed to reflux. After refluxing overnight, the solvent was evaporated and the concentrate was treated with water. The aqueous mixture was extracted three times with EtOAc. The EtOAc extracts were combined, washed with saturated aqueous NaCl, and dried over anhydrous $Na_2SO_4$. The drying agent was removed by filtration and the filtrate was evaporated at reduced pressure affording a pale yellow oil which was purified by chromatography and kugel rohr distillation, affording a pale yellow oil: bp=190°-197° C. (0.3 mm).

EXAMPLE 6

4-Methyl-5-methylthio-3-(2-naphthyl)-4H-1,2,4-triazole

A mixture of 2,4-dihydro-4-methyl-5-(2-naphthyl)-3H-1,2,4-triazole-3-thione (5.26 g, $2.18 \times 10^{-2}$ mole), $K_2CO_3$ (3.01 g, $2.18 \times 10^{-2}$ mole), methyl iodide (1.5 ml, $2.4 \times 10^{-2}$ mole), and acetone (65 ml) was stirred and warmed to reflux. After refluxing overnight, the solvent was evaporated at reduced pressure and the concentrate was treated with water. The aqueous mixture was extracted with EtOAc three times. The EtOAc extracts were combined, washed with saturated aqueous NaCl, and dried over anhydrous $Na_2SO_4$. The drying agent was removed by filtration and the filtrate was evaporated at reduced pressure to yield the desired product. Crystallization from EtOAc afforded colorless plates, Mp 177°-179° C.

EXAMPLE 7

3-(2-Fluorophenyl)-4-methyl-5-methylsulfinyl-4H-1,2,4-triazole

To a stirred, 0° C., solution of 3-(2-fluorophenyl)-4-methyl-5-methylthio-4H-1,2,4-triazole (5.0 g, $2.2 \times 10^{-2}$ mole) and $CH_2Cl_2$ (125 ml) was added portionwise m-chloroperoxybenzoic acid (4.83 g, $2.24 \times 10^{-2}$ mole, 80% active MCPBA). After stirring overnight at room temperature, the reaction was diluted with $CH_2Cl_2$ until homogeneous and was then washed in turn twice with saturated aqueous $NaHCO_3$ and once with saturated aqueous NaCl. After drying over anhydrous Na$_2$SO$_4$, the CH$_2$Cl$_2$ was evaporated leaving an oil which slowly crystallized. Crystallization from EtOAc/hexane gave a colorless solid: Mp 95°–97° C.

EXAMPLE 8

4-Methyl-5-methylsulfinyl-3-(2-naphthyl)-4H-1,2,4-triazole

To a stirred, 0° C., solution of 4-methyl-5-methylthio-3-(2-naphthyl)-4H-1,2,4-triazole (4.00 g, 1.57×10$^{-2}$ mole) and CH$_2$Cl$_2$ (110 ml) was added portionwise m-chloroperoxybenzoic acid (3.38 g, 1.57×10$^{-2}$ mole). overnight at room temperature the reaction was diluted with CH$_2$I$_2$ (200 ml), washed two times with saturated aqueous NaHCO$_3$ and one time with saturated aqueous NaCl, and dried over anhydrous Na$_2$SO$_4$. The drying agent was removed by filtration and the filtrate was evaporated at reduced pressure leaving an off-white solid which was purified by flash chromatography (4% CH$_3$OH/CH$_2$Cl$_2$). Crystallization from toluene afforded small colorless plates: Mp 224°–226° C.

EXAMPLE 9

3-(2-Fluorophenyl)-4-methyl-5-methylsulfonyl-4H-1,2,4-triazole

To a stirred, 0° C., solution of 3-(2-fluorophenyl)-4-methyl-5-methylthio-4H-1,2,4-triazole (5.0 g, 2.2×10$^{-2}$ mole) and CH$_2$Cl$_2$ (125 ml) was added portionwise m-chloroperoxybenzoic acid (12.1 g, 5.6×10$^{-2}$ mole, 80% active MCPBA). After stirring overnight at room temperature, the reaction was diluted with CH$_2$Cl$_2$ until homogeneous and was then washed in turn twice with saturated aqueous NaHCO$_3$ and once with saturated aqueous NaCl. After drying over anhydrous Na$_2$SO$_4$, the CH$_2$Cl$_2$ was evaporated at reduced pressure leaving a solid which was purified by chromatography and subsequent crystallization from EtOAc/hexane giving colorless matted needles: Mp 128°–130° C.

EXAMPLE 10

4-Methyl-5-methylsulfonyl-3-(2-naphthyl)-4H-1,2,4-triazole

To a stirred, 0° C., solution of 4-methyl-5-methylthio-3-(2-naphthyl)-4H-1,2,4-triazole (5.62 g, 2.20×10$^{-2}$ mole) and CH$_2$Cl$_2$ (125 ml) was added portionwise m-chloroperoxybenzoic acid (12.1 g, 5.6×10$^{-2}$ mole, 80% active MCPBA). The reaction was stirred at 0° C. for 1 hour and then allowed to warm to room temperature. After stirring overnight, the reaction was diluted with CH$_2$Cl$_2$ until homogeneous. The CH$_2$Cl$_2$ solution was then washed in turn with saturated aqueous NaHCO$_3$ and saturated aqueous NaCl. After drying over anhydrous Na$_2$SO$_4$, the CH$_2$Cl$_2$ was evaporated at reduced pressure to afford the desired product, which was recrystallized from ethanol affording off-white plates, Mp 204°–206° C.

EXAMPLE 11

1-Benzoyl-4-methylthiosemicarbazide

To a stirred solution of benzoic acid hydrazide (2.35 g, 1.73×10$^{-2}$ mole) and THF (50 ml) was added a solution of methyl isothiocyanate (1.14 g, 1.56×10$^{-2}$ mole) and THF (50 ml). The reaction was then refluxed for 2 hours before being cooled. The precipitate was collected by filtration and crystallized from ethanol, affording a colorless solid, Mp 199°–200° C.

EXAMPLE 12

4-Methyl-5-phenyl-2,4-dihydro-3H-1,2,4-triazole-3-thione

A stirred mixture of 1-benzoyl-4-methylthiosemicarbazide (20.9 g, 1.00×10$^{-1}$ mole) and 1 molar aqueous NaHCO$_3$ (1000 ml, 1 mole) was heated to reflux. After refluxing overnight the reaction was cooled in an ice bath. With stirring the solution was carefully acidified by the dropwise addition of conc. HCl (92 ml, 1.1 mole). A colorless precipitate formed and this was subsequently collected by filtration. Crystallization from ethanol afforded colorless, chunky crystals, Mp 164°–166° C.

Literature reference

G. Young and W. J. Oates, *J. Chem. Soc.*, 79, G59 (1901).

EXAMPLE 13

4-Methyl-3-phenyl-5-methylthio-4H-1,2,4-triazole

To a stirred solution of 4-methyl-5-phenyl-2,4-dihydro-3H-1,2,4-triazole-3-thione (5.0 g, 2.6×10$^{-2}$ mole) and 1 molar aqueous NaOH (59 ml, 5.9×10$^{-2}$ mole) was added a solution of methyl iodide (2.6 ml, 4.2×10$^{-2}$ mole) and ethanol (13 ml). The reaction was stirred for 3 hours and it was then placed in the refrigerator. After standing in the refrigerator overnight, the precipitate was collected by filtration. Crystallization from isopropanol afforded colorless needles, Mp 134°–135° C.

Literature reference

E. Hoggarth, *J. Chem. Soc.*, 1918 (1949).

EXAMPLE 14

4-Methyl-3-phenyl-5-methylsulfonyl-4H-1,2,4-triazole

To a stirred, 0° C., mixture of 4-methyl-3-phenyl-5-methylthio-4H-1,2,4-triazole (4.2g, 2.05×10$^{-2}$ mole) and CH$_2$Cl$_2$ (120 ml) was added portionwise MCPBA (11.0 g, 5.1×10$^{-2}$ mole, 80% active MCPBA). After 30 minutes, the cooling bath was removed. After stirring overnight the reaction was diluted with CH$_2$Cl$_2$ (120 ml) and the resultant mixture was transferred to a separatory funnel where it was washed twice with saturated aqueous NaHCO$_3$ and once with saturated aqueous NaCl. After drying over anhydrous Na$_2$SO$_4$, the CH$_2$Cl$_2$ was evaporated at reduced pressure affording the crude product which was purified by flash chromatography (20% EtOAc/CH$_2$Cl$_2$) and crystallization from EtOAc/hexane affording colorless crystals, Mp 158°–160° C.

By substituting the appropriate acid chlorides in the procedure of Example 1 or by substituting the appropriate acid hydrazides and isothiocyanates in the procedure of. Example 11 and reacting the resulting thiosemicarbazide according to the procedures of Examples 3, 5, 7 and 9, the tabulated compounds of Formula I are obtained.

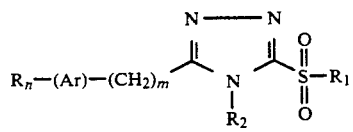

| $R_n$—(Ar)—(CH$_2$)$_m$ | q | R$_1$ | R$_2$ | mp (°C.) |
|---|---|---|---|---|
| phenyl | 0 | CH$_3$ | CH$_3$ | 134–136 |
| phenyl | 1 | CH$_3$ | CH$_3$ | 144–146 |
| phenyl | 0 | C$_2$H$_5$ | CH$_3$ | 94–99 |
| phenyl | 1 | C$_2$H$_5$ | CH$_3$ | 131–133 |
| phenyl | 2 | C$_2$H$_5$ | CH$_3$ | 141–143 |
| 4-fluorophenyl | 0 | CH$_3$ | H | 145–146 |
| 4-fluorophenyl | 0 | CH$_3$ | CH$_3$ | 193–195 |
| 3-fluorophenyl | 0 | CH$_3$ | CH$_3$ | 151–153 |
| 3-fluorophenyl | 2 | CH$_3$ | CH$_3$ | 175–177 |
| 2-fluorophenyl | 0 | CH$_3$ | C$_2$H$_5$ | oil |
| 2-fluorophenyl | 0 | C$_2$H$_5$ | CH$_3$ | 95–97 |
| 2-fluorophenyl | 1 | C$_2$H$_5$ | CH$_3$ | 63–67 |
| 2-fluorophenyl | 2 | C$_2$H$_5$ | CH$_3$ | 145–147 |
| 2-chlorophenyl | 0 | CH$_3$ | CH$_3$ | oil |
| 4-chlorophenyl | 0 | CH$_3$ | CH$_3$ | 105–107 |
| 4-chlorophenyl | 0 | CH$_3$ | C$_2$H$_5$ | 113–115 |
| 4-methoxyphenyl | 0 | CH$_3$ | CH$_3$ | 149–151 |
| 4-methoxyphenyl | 1 | CH$_3$ | CH$_3$ | 168–170 |
| 4-methoxyphenyl | 2 | CH$_3$ | CH$_3$ | 187–189 |
| 4-tolyl | 0 | CH$_3$ | CH$_3$ | 140–142 |
| 4-tolyl | 1 | CH$_3$ | CH$_3$ | 161–163 |
| 4-tolyl | 2 | CH$_3$ | CH$_3$ | 170–172 |

What is claimed is:

1. A compound of the formula

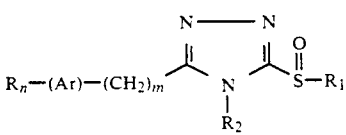

wherein Ar is phenyl or naphthyl;
R1 is C$_{1-6}$ lower alkyl;
R2 is hydrogen or C$_{1-6}$ alkoxy, hydroxy, halogeno or trifluoromethyl and n is zero, 1 or 2, or R$_n$—(Ar)— is methylenedioxyphenyl; and
m is zero, 1 or 2;
or a pharmaceutically acceptable salt thereof.

2. A compound of claim 1 wherein Ar is phenyl.

3. A compound of claim 2 wherein m is zero.

4. A compound of claim 3 which is 4-methyl-3-phenyl-5-ethylsulfinyl-4H-1,2,4triazole.

5. A compound of claim 1 wherein n is zero or one, m is zero, R is halogeno, and R$_1$ and R$_2$ are independently methyl or ethyl.

6. A compound of the formula wherein
Ar is phenyl or naphthyl;
R$_1$ is C$_{1-6}$ lower alkyl;
R$_2$ is hydrogen or C$_{1-6}$ lower alkyl;
R is C$_{1-6}$ lower alkyl, C$_{1-6}$ alkoxy, hydroxy, halogeno, or trifluoromethyl, and n is zero, 1 or 2, or R$_n$—(Ar)— is methyenedioxyphenyl; and
m is zero, 1 or 2; or a pharmaceutically acceptable salt thereof;
with the provisos that (1) R$_n$—(Ar)—(CH$_2$)$_m$ is other than 2-ethoxyphenyl); (2) when R$_n$—Ar—(CH$_2$)$_m$ represents phenyl and R$_1$ represents methyl, R$_2$ is C$_{1-6}$ lower alkyl; and (3) when R$_n$—(Ar)—CH$_2$)$_m$ represents 4-chlorophenyl, R$_2$ is other than ethyl.

7. A compound of claim 6 wherein Ar is phenyl.

8. A compound of claim 7 wherein m is zero.

9. A compound of claim 8 which is 4-methyl-3-phenyl-5-methylsulfonyl-4H-1,2,4-triazole.

10. A compound of claim 8 which is 4-methyl-3-phenyl-5-ethylsulfonyl-4H-1,2,4-triazole.

11. A compound of claim 6 wherein n is zero or one, m is one, R is halogeno and R$_1$ and R$_2$ are independently methyl or ethyl.

12. A compound of claim 11 which is 3-(2-fluorophenyl)-4-methyl-5-methylsulfonyl-4H-1,2,4-triazole.

* * * * *